United States Patent
Rains et al.

[11] Patent Number: 6,140,538
[45] Date of Patent: Oct. 31, 2000

[54] PROCESS FOR PREPARING 4-AMINODIPHENYLAMINES

[75] Inventors: Roger Keranen Rains, Richfield; Ralph Albert Genetti; Edward Albert Lambers, both of Copley, all of Ohio; Antonius Johannes van Hengstum, Deventer, Netherlands

[73] Assignee: Flexsys America L.P., Akron, Ohio

[21] Appl. No.: 09/243,719

[22] Filed: Feb. 3, 1999

Related U.S. Application Data

[60] Provisional application No. 60/085,887, May 18, 1998.

[51] Int. Cl.$^7$ .................................................. C07C 209/00
[52] U.S. Cl. .............................................................. 564/416
[58] Field of Search .............................................. 564/416

[56] References Cited

U.S. PATENT DOCUMENTS

| | | |
|---|---|---|
| 4,463,191 | 7/1984 | D'Sidocky et al. . |
| 5,117,063 | 5/1992 | Stern et al. . |
| 5,608,111 | 3/1997 | Stern et al. . |
| 5,739,403 | 4/1998 | Reinartz et al. . |
| 5,840,982 | 11/1998 | Reynolds et al. . |

FOREIGN PATENT DOCUMENTS

| | | |
|---|---|---|
| 1100440A | 3/1995 | China . |
| 0 184 914 | 6/1986 | European Pat. Off. . |
| 0 863 130 | 9/1998 | European Pat. Off. . |
| 196 00 722 | 7/1997 | Germany . |
| WO 93/00324 | 1/1993 | WIPO .......................... C07C 209/02 |
| WO 98/56751 | 12/1998 | WIPO .......................... C07C 209/36 |

OTHER PUBLICATIONS

*Catalytic Hydrogenation Reactions*—The Effect of Water on Catalyst Activity, 2 pgs.
*Research Disclosure*, Process for N–Alkyl–N–Aryl–p–Phenylenediamines, Mar. 1998, No. 407,2 pgs.
*J. Chem. Soc., Chem. Commun.*, Heterogeneous Catalytic Transfer Hydrogenation of 4–Nitrodiphenylamine to p–Phenylenediamines, 1988, pp. 1275–1276.

*Primary Examiner*—Paul J. Killos
*Attorney, Agent, or Firm*—Louis A. Morris

[57] ABSTRACT

A process for preparing an optionally substituted 4-aminodiphenylamine comprising reacting an optionally substituted aniline and an optionally substituted nitrobenzene in the presence of water and a base while controlling the water content so as to ensure a molar ratio of water to the base charged of not less than about 4:1 at the start of the coupling reaction and not less than about 0.6:1 at the end of the coupling reaction to produce 4-nitrodiphenylamine and/ or 4-nitrosodiphenylamine and/or salts thereof. The coupling reaction is followed by a hydrogenation reaction where the coupling reaction product is hydrogenated in the presence of a hydrogenation catalyst and added water so as to ensure a molar ratio of total water to base of at least about 4:1 at the end of hydrogenation. Aqueous and organic phases are obtained and the optionally substituted 4-aminodiphenylamine recovered from the organic phase.

40 Claims, No Drawings

PROCESS FOR PREPARING 4-AMINODIPHENYLAMINES

This patent claims priority of U.S. Provisional No. 60/085,887, filed May 18, 1998.

BACKGROUND OF THE INVENTION

1. Field of the Invention

The present invention relates to a process for preparing 4-aminodiphenylamines. It also relates to a process for preparing alkylated derivatives of said 4-aminodiphenylamines.

2. Related Art

4-Aminodiphenylamines are widely used as intermediates in the manufacture of alkylated derivatives having utility as antiozonants and antioxidants, as stabilizers for monomers and polymers, and in various specialty applications. For example, reductive alkylation of 4-aminodiphenylamine (4-ADPA) with methylisobutyl ketone provides N-(1,3-dimethylbutyl)-N'-phenyl-p-phenylene-diamine, which is a useful antiozonant for the protection of various rubber products.

4-Aminodiphenylamines can be prepared in various ways. An attractive synthesis is the reaction of an optionally substituted aniline with an optionally substituted nitrobenzene in the presence of a base followed by catalytic hydrogenation of the reaction product, as disclosed, for example, in U.S. Pat. No. 5,608,111 (to Stern et al.) and U.S. Pat. No. 5,739,403 (to Reinartz et al.).

U.S. Pat. No. 5,608,111 describes a process for the preparation of an optionally substituted 4-ADPA wherein optionally substituted aniline and optionally substituted nitrobenzene are reacted (coupled) in the presence of a base. Subsequently, water is added to the coupling product and the resulting reaction mixture is catalytically hydrogenated. The catalyst, which typically is a supported noble metal catalyst, is removed from the hydrogenation reaction mixture, the organic phase is separated in order to isolate the 4-ADPA, and the aqueous phase, which contains the base, is returned to another cycle of the initial reaction mixture. In working examples, aniline and nitrobenzene are reacted in the presence of tetramethylammonium hydroxide as the base, and water and aniline are azeotropically removed during the coupling reaction.

U.S. Pat. No. 5,739,403 describes a process for a coupling reaction comparable to Example 13 of U.S. Pat. No. 5,608,111 and subsequent catalytic hydrogenation, where the amount of water added is 25 to 80 wt. % relative to the weight of the coupling (condensation) reaction mixture. Example 1 of U.S. Pat. No. 5,739,403 is distinguished from Example 13 of U.S. Pat. No. 5,608,111 in that it teaches a 4-hour hold period, with continued distillation, after completion of nitrobenzene addition. After the hydrogenation, toluene is added, the catalyst is filtered out, and the organic and aqueous phases are separated. In Example 1 it is stated that, "Analysis of the aqueous phase shows that 99.7% of the introduced tetramethylammonium hydroxide may be isolated. The resultant aqueous phase may be returned to the reaction without loss of reactivity."

One of the objectives of the present invention is that of base recovery and of recycling the base. U.S. Pat. No. 5,739,403 provides no teaching with regard to recycling the base with as little loss of reactivity as possible (including effect on hydrogenation catalyst activity). Since the document does not disclose a second cycle of coupling and hydrogenation reactions, the reactivity of the base recovered in the process disclosed is in fact unknown.

A further disadvantage of the process disclosed in U.S. Pat. No. 5,739,403 is that a relatively large amount of an aromatic solvent is used for separating the organic and aqueous phases. The use of large amounts of an organic solvent in unit operations like separation of layers is highly undesirable in commercial scale processes because of the costs involved in recovering and processing such solvent. Therefore, another objective of the present invention is to facilitate separation of the organic and aqueous phases.

Another objective of the present invention is that of recycling the hydrogenation catalyst and the excess aniline. None of the references cited above touches upon this feature.

A further objective of the present invention is that of handling the formation of any by-products, such as azobenzene and azoxybenzene, which may or may not occur.

SUMMARY OF THE INVENTION

Accordingly, in brief summary, the present invention is in one embodiment a process for preparing an optionally substituted 4-aminodiphenylamine which comprises:

(i) reacting an optionally substituted aniline and an optionally substituted nitrobenzene in the presence of water and a base, while controlling the amount of water in relation to the base so as to ensure a molar ratio of water to the base charged of not less than about 4:1 at the start of the coupling reaction and not less than about 0.6:1 at the end of the coupling reaction to produce 4-nitrodiphenylamine and/or 4-nitrosodiphenylamine and/or salts thereof;

(ii) hydrogenating the reaction product of step (i) in the presence of a hydrogenation catalyst and added water so as to ensure a molar ratio of total water to base of at least about 4:1 at the end of hydrogenation;

(iii) separating the hydrogenation catalyst from the reaction mixture;

(iv) obtaining an aqueous phase and organic phase from the reaction mixture, separating the organic phase from the aqueous phase, recovering any excess of the optionally substituted aniline from the organic phase and isolating the optionally substituted 4-aminodiphenylamine from the remaining organic phase.

In another embodiment the present invention comprises the above steps (I) through (iv) plus the further steps comprising:

(v) reusing the aqueous phase and any recovered excess of the optionally substituted aniline to form a subsequent step (i) reaction mixture;

(vi) reusing the hydrogenation catalyst in a subsequent step (ii) hydrogenation; and, (vii) hydrogenating the azobenzene and/or azoxybenzene which may be produced during step (I) and/or step (ii) to aniline and isolating the aniline for reuse in a subsequent step (i) reaction mixture together with recovered excess aniline in (v).

Other embodiments of the present invention encompass details about flow schemes and reaction mixtures, all of which are hereinafter disclosed in the following discussion of each of the facets of the present invention.

DETAILED DESCRIPTION OF THE INVENTION

The present invention is directed to a process for making 4-ADPA that is economically attractive. More in particular, and in a first embodiment, the invention provides a process in which the base, the aniline and the hydrogenation catalyst are recycled in a manner which makes the process economically attractive. It has been found that the base and the aniline can be recycled with a minimum loss of reactivity for coupling of aniline with nitrobenzene and that the hydrogenation catalyst can be recycled with a minimum loss of reactivity as well, by controlling the level of impurities in the recycle streams and by carefully controlling the amount of water in relation to the base during each of the two reaction steps. It has further been found that the use of undesirable amounts of an organic solvent like toluene in the separation step can be dispensed with by addition of water after the hydrogenation step, before filtration, to recover catalyst for recycle and by appropriate choice of equipment for the liquid-liquid separation.

For example, if during the coupling reaction the amount of water in relation to the base is not controlled as carefully as it should be under the invention process, erratic hydrogenation results will ensue in the commercial production of 4-ADPA in terms of yield and/or catalyst usage and/or reaction time. It has been determined that if too little water is left at the end of the coupling reaction, decomposition of the base takes place. It has also been determined that use of a long hold period with continued distillation, to achieve the end of reaction is detrimental, in that it further increases base decomposition. The base decomposition products can generate compounds, such as formaldehyde and formaldehyde reaction products, which can act as a poison for the hydrogenation catalyst. Since these compounds are carried over into the hydrogenation reactor, the hydrogenation catalyst will be poisoned in a manner that cannot be predicted. In consequence, catalyst activity will vary unpredictably also. This is unacceptable in a process which is to have commercial utility, since clearly the amount of catalyst loading required for each batch to achieve a reasonably short uniform hydrogenation cycle from batch to batch should be reliably known beforehand. It is to be understood that the precise minimum amount of water in relation to the base that is required to protect the base, depends on the actual base used, since tetraalkylammonium hydroxides and related compounds, such as carbonates, vary in their thermal stability.

On the other hand, if too much water is left at the end of the coupling reaction, the reaction yield is reduced due to increased formation of by-products, such as azobenzene, and/or increased levels of unreacted nitrobenzene. This can be economically unattractive, because the higher amount of water and the higher level of by-products and/or nitrobenzene increase the equipment size for coupling, hydrogenation, separation, distillation and by-product recovery. However, it may be advantageous to leave somewhat more water at the end, to the extent that base decomposition is reduced, since the unreacted nitrobenzene can be recovered as azobenzene and aniline in the step (ii) and step (vii) hydrogenations. The skilled person can determine the practical upper limit for a given commercial process.

It is the experience of the present inventors that in carrying out the reaction on a plant scale, there is always some decomposition of base during the coupling reaction step. This decomposition is also observed on lab and pilot plant scale. Therefore, an overall recovery of "99.7% of the introduced tetramethylammonium hydroxide" as mentioned in the above prior art is unrealistic. It is more likely that this recovery efficiency referred to recovery of TMAH from the final hydrogenation batch, since a 0.3% loss of the TMAH to the organic phase is realistic. It is further the experience of the present inventors that in carrying out the reaction on a plant scale, there is often some loss of reactivity of the recycle base, that causes lower yield (selectivity) for the condensation of aniline with nitrobenzene. Furthermore, the coupling reaction mixture made with recycle base can require substantially more catalyst for the hydrogenation step vs. fresh base. These effects, due to impurities dissolved in the recycle base stream, are also observed on lab and pilot plant scale.

The working examples of U.S. Pat. No. 5,739,403 are consistent with poisoning of the noble metal catalyst as being the result of having too little water at the end of the coupling reaction, considering the relatively large amount of hydrogenation catalyst used in the examples (viz., about 1.21 milligram atoms of Pt per mole of nitro/nitroso compounds; assuming the same 95.5% yield from nitrobenzene as Example 13 of U.S. Pat. No. 5,608,111, since it is similar to the U.S. Pat. No. 5,739,403 working examples), the long hydrogenation reaction time (4 hours), and the strong variation in yields (ranging from 82 to 92%). A skilled practitioner can calculate the amount of water remaining in the batch of Example 13 in U.S. Pat. No. 5,608,111 at the end of nitrobenzene feed, from literature data for the water/aniline azeotrope at the operating pressure and the advice in the example on how much azeotrope to remove during nitrobenzene feed. Since Example 1 in U.S. Pat. No. 5,739,403 is essentially a copy of the above mentioned Example 13 up to the end of nitrobenzene feed, one can conclude that the calculated final water content for Example 13 applies as well to Example 1 at the end of nitrobenzene feed. This calculated water content corresponds to a Water/TMAH molar ratio of about 0.3:1. Since this is the starting point for the 4 hour hold period in Example 1, during which the distillation of water/aniline azeotrope was continued, the final water content for Example 1 can be expected to be well below a Water/TMAH molar ratio of 0.3:1. The excessive base decomposition expected from this mode of operation easily explains the high catalyst charge and long hydrogenation time demonstrated by Example 1 of U.S. Pat. No. 5,739,403.

It has further been found that a certain minimum amount of water in relation to the base during the hydrogenation reaction is also critical if the process is to have commercial utility. The base is liberated during the hydrogenation of the 4-nitro- and/or 4-nitrosodiphenylamine salts and ends up in the aqueous phase. It has been found that in this aqueous phase the liberated base must be present in an amount, which does not exceed a maximum level, as further described below. The molar ratio of total water to base at the end of hydrogenation should be at least about 4:1, although It is to be understood that the precise minimum amount of water in relation to the base that is required to protect the base, depends on the actual base used, since tetraalkylammonium hydroxides and related compounds, such as carbonates, vary in their thermal stability.

Acceptable nitrobenzene selectivity can be obtained with nitrobenzene addition time not exceeding 180 minutes. In general, the addition time should be as fast as possible, consistent with capability to remove water by distillation. Shorter addition time, such as 80 to 100 minutes, favors lower base decomposition and the shorter overall cycle time reduces equipment size. It is acceptable to add part or all of the aniline concurrently with the nitrobenzene.

Typical examples of substituted anilines that may be used in accordance with the process of the present invention include but are not limited to 2-methoxyaniline, 4-methoxyaniline, 4-chloroaniline, p-toluidine, 4-nitroaniline, 3-bromoaniline, 3-bromo-4-aminotoluene, p-aminobenzoic acid, 2,4-diaminotoluene, 2,5-dichloroaniline, 1,4-phenylene diamine, 4,4'-methylene dianiline, 1,3,5-triaminobenzene, and mixtures thereof.

Typical examples of substituted nitrobenzenes that may be used in accordance with the process of the present invention include but are not limited to o- and m-methylnitrobenzene, o- and m-ethyinitrobenzene, o- and m-methoxynitrobenzene, and mixtures thereof.

Although the process of the present invention is useful for preparing substituted 4-ADPA, i.e. starting from a substituted aniline and/or a substituted nitrobenzene, the invention process will hereinafter be described with reference to the manufacture of 4-ADPA itself, starting from aniline and nitrobenzene.

Typically, the molar ratio of aniline to nitrobenzene in the process according to the present invention is from about 1:1 to about 10:1. Preferably, it ranges from about 3:1 to about 7:1.

The base typically is a tetraalkylammonium hydroxide. Examples include but are not limited to tetramethylammonium hydroxide, tetrapropylammonium hydroxide, benzyltrimethylammonium hydroxide, tetrabutylammonium hydroxide, phenyltrimethylammonium hydroxide, carbonate salts of any of the foregoing and mixtures thereof. Preferably, the base is tetramethylammonium hydroxide. For practical purposes, it is preferred to start from a commercially available 25 weight per cent aqueous solution of tetramethylammonium hydroxide. In forming the step (i) reaction mixture, the base can either be added as the ammonium hydroxide or it can be generated in situ by employing a combination of a tetraalkylammonium halide and an alkali metal hydroxide such as, for example, a combination of tetramethylammonium bromide and sodium or potassium hydroxide.

During the reaction between aniline and nitrobenzene, i.e. step (i), water is distilled off and the molar ratio of water to base is carefully controlled. It is to be noted that the water may be distilled off in the form of a water/aniline azeotrope if and when aniline is present in the reactor in a molar excess relative to nitrobenzene in the reactor. Preferably, the molar ratio of water to base is not less than about 4.5:1 at the start of the coupling reaction, which is the point in time at which the aniline, nitrobenzene, and base come into reactive contact with each other, and not less than about 1.0:1 at the end of the coupling reaction, which is the point in time at which at most 2.0% of the limiting reagent, which typically is nitrobenzene, normally remains unreacted in the batch. Depending on how well the rate of water removal is controlled, a hold period could be required after the end of nitrobenzene feed to complete water removal and/or reaction. The progress of the preliminary water removal steps and the coupling reaction can be monitored by measuring the amount of water removed by distillation. This can be done by measuring the weight or volume of water in the distillate, with allowance for the amount of aniline in the distillate. It is also possible to monitor water directly in the coupling batch by an instrumental method, such as Infrared spectroscopy. It is further possible to monitor the reaction directly for nitrobenzene in the coupling reactor by an instrumental method, such as Infrared spectroscopy.

It is to be understood that for calculation purposes the amount of base is the total amount of base present in the reactor, that is free base and/or base included in the 4-nitroso- and/or 4-nitrodiphenylamine salts. The amount of water includes the water that hydrates with the base and/or with other compounds formed in the process.

The molar ratio of base to nitrobenzene may be in the range of about 0.7 to about 4:1, preferably in the range of about 0.9:1 to about 1.5:1.

Conditions of temperature and pressure during the coupling reaction and during the preliminary water removal steps include temperatures in the range of about 10° to about 150° C., preferably about 50° to about 100° C., and pressures in the range of about 20 to about 200 mbar, preferably in the range of about 50 to about 150 mbar. Routine experimentation within these ranges will enable the skilled person to achieve a rate of water removal in keeping with the parameter values in accordance with the invention process. Coupling reaction time, including the time for nitrobenzene addition plus any hold time but not including the preliminary water removal steps, should be less than about 3.5 hours. The reaction mixture is agitated during the entire coupling reaction. Agitation is recommended during water removal after aniline addition and is optional during water removal before aniline addition.

Conditions of temperature and pressure during the step (ii) hydrogenation reaction include temperatures in the range of about 50° to about 150° C., preferably about 50° to about 100° C., and pressures in the range of about 1 to about 25 barg, preferably in the range of about 3 to about 20 barg. Routine experimentation within these ranges will enable the skilled person to achieve attractive hydrogenation rates. The need for agitation of the reaction mixture depends on the type of reactor used. The most common situation is for the reactor to have mechanical agitation. However, another type of reactor circulates the reaction mixture through a heat exchanger for heat removal and back to the reactor through an eductor. In this case, the liquid returning at a high volumetric flow rate agitates the bulk liquid in the reactor proper. Yet another reactor type, called a gas lift reactor, circulates a high volumetric flow of hydrogen to provide agitation.

Carrying out the step (ii) hydrogenation reaction requires the addition to the coupling reaction mixture of water and hydrogenation catalyst. Enough water must be used to protect base from significant levels of thermal decomposition in the hydrogenation reactor. Addition of water also improves the activity of recycled catalyst. However, when the coupling reaction is done according to this process, increasing the water charge does not improve activity of fresh catalyst, contrary to the implication in U.S. Pat. No. 5,739,403 in the statement that "It is particularly significant that the hydrogenation according to the invention, in which a higher content of water is used than in the prior art, provides a considerably shorter reaction time . . . ".

The amount of water added for the hydrogenation reaction must be such as to ensure that the molar ratio of total water to base at the reaction end is at least about 4:1 and preferably at least about 6:1. It is to be understood that total water means the sum of the water left after the coupling reaction and the water added for the hydrogenation reaction. It is further to be understood that for calculation purposes the amount of base is to be taken as total base present at the beginning of the hydrogenation reaction, that is: free base (if any), base included in the 4-nitroso- and/or 4-nitrodiphenylamine salts and any impurity compounds that liberate base upon hydrogenation.

The hydrogenation may be carried out using a supported noble metal catalyst, such as rhodium-on-carbon, ruthenium-on-carbon, platinum-on-carbon, palladium-on-carbon, or mixtures of precious metals-on-carbon, or other conventional hydrogenation catalysts, such as Raney nickel or Raney copper. Other supports may be employed, such as alumina for Pd, Pt, Rh, Ru and mixed metal catalysts. Preferred catalysts are platinum-on-carbon or palladium-on-carbon. However, the choice of catalyst is not limited to any of those named. Catalytic hydrogenations using a noble metal catalyst are well-known in the art and are described in detail in *Catalytic Hydrogenation in Organic Synthesis*, P. N. Rylander, Academic Press, New York, 1979, p. 299 and other readily available texts. Without catalyst recycle the amount of fresh catalyst added in the hydrogenation step is such that, per mole of 4-nitroso- and/or 4-nitrodiphenylamine compounds, 0.01 to 0.75 milligram atoms of metal, preferably 0.01 to 0.5 milligram atoms of metal, and most preferably 0.01 to 0.25 milligram atoms of metal are present. With catalyst recycle the residual activity of the recycled mass can range from very low to high enough to skip one or more additions of fresh catalyst. However, even recycle catalyst of very low residual activity gives a shorter hydrogenation time in combination with fresh catalyst than the same amount of fresh catalyst alone. Therefore, with catalyst recycle, even after repeated catalyst use cycles, the amount of fresh catalyst added to the recycled catalyst mass in the hydrogenation step is such that, per mole of 4-nitroso- and/or 4-nitrodiphenylamine compounds, 0.0 to 0.4 milligram atoms of new metal, preferably 0.0 to 0.25 milligram atoms of new metal, and most preferably 0.0 to 0.15 milligram atoms of new metal are present. Weight ratios of 1:1 and higher for recycle catalyst mass to fresh catalyst intake are preferred, but any amount of recycle catalyst can be beneficial.

The invention process allows for short hydrogenation times, not only in the first cycle, but also over many more, for example every cycle. Hydrogenation times of less than 4 hours, preferably less than 3 hours, more preferably less than 2 hours, and most preferably less than 1.5 hour are readily realized within the invention process parameter ranges. Completion of the hydrogenation is indicated when hydrogen uptake and heat generation reach prescribed minimum values, which can be determined by one skilled in the art for any given reactor system and coupling reaction mass composition.

Fresh catalyst intake may also be reduced by pretreatment of the step (ii) feed, even with low activity recycle catalyst, by contacting the feed with the catalyst under hydrogen at a temperature of from about about 50° C. to about 150° C. and a hydrogen pressure of from about 1 to about 25 barg.

After completion of the hydrogenation reaction the catalyst is separated from the reaction mixture and the liquid organic and aqueous phase layers are separated. Optionally, water may be added to the reaction product in order to ease filtration as well as separation between the organic phase and the aqueous phase. The latter phase contains the base. This option is especially preferred if the amount of water employed during the hydrogenation reaction is insufficient to allow easy layer separation. For a water to base mole ratio below 9.4 (i.e. above about 35 wt. % base in the aqueous phase) extra water and/or an organic solvent will most likely be required for efficient filtration and phase separation. At a mole ratio of 12.3:1 (29 wt. % base), it would probably not be necessary to add extra water for efficient filtration and phase separation. However, in any case (unless the recycle base is weak, such as 21 wt. % or lower) it is necessary to extract the organic phase with extra water to reduce the amount of base and base salts that go forward to distillation. These compounds decompose and react in the distillation system to make an impurity that cannot be easily separated from 4-ADPA by distillation. Thus, some combination of water addition and/or extraction after hydrogenation is probably necessary. An organic solvent can be used at any water level to enhance phase separation and to reduce 4-ADPA in the recycle base by increasing the distribution to the organic phase. However, the preferred process when operated properly does not need the organic solvent.

It is also possible to add the water after separating the catalyst from the reaction mixture, unless a high base content would make the batch too viscous for efficient filtration and thus require dilution with water.

Following layer separation, it might be necessary or desirable to reduce the water to base molar ratio in the aqueous phase for reuse of the aqueous phase in a subsequent step (i) reaction. This could be accomplished by distilling off water or by adding fresh concentrated base, or a combination of water distillation and fresh base addition. It is possible to generate concentrated base solution in a separate vessel from the coupling reactor or in a preliminary step in the coupling reactor, as described in the typical lab preparation procedure. To maintain base reactivity for the coupling reaction and catalyst activity for the hydrogenation reaction, it is important to control the level of impurities in the recycle base. This is done by efficient separation of the aqueous and organic phases in step (iv), by control of impurity formation in the step (i) coupling reactor, most particularly by maintaining operation above a minimum water content during the coupling reaction, by a maximum coupling reaction time (nitrobenzene feed plus hold), by control of impurity formation in the step (ii) hydrogenation reactor, most particularly by maintaining operation above a minimum water content during the hydrogenation batch cycle and by minimizing the amount of impurities such as 4-ADPA, methanol and catalyst in recycle base and recycle aniline.

The aqueous phase is reused to form a new step (i) reaction mixture. Fresh base is added to replace base lost by decomposition, by-product formation and solubility in the separated organic phase, but depending on how the aqueous phase is processed, the addition of fresh base may be minimal or only periodically necessary. Excess Aniline recovered by distillation from the organic product phase, by distillation from the azobenzene/azoxybenzene conversion to aniline and from the coupling reactor distillate is combined with make-up fresh aniline for recycle to form a new step (i) reaction mixture. The hydrogenation catalyst can be reused for a new step (ii) hydrogenation with fresh catalyst addition as needed.

There is, in fact, a beneficial effect of using fresh catalyst together with a mass of recycle catalyst that has low residual activity. It has been found that the use of such recycle catalyst with a smaller fresh catalyst intake will produce a shorter hydrogenation time. Without recycle catalyst a greater fresh catalyst intake would be needed to obtain the same hydrogenation time.

It has been found that 4-ADPA and methanol contained in recycle aniline and recycle base are critical impurities for the coupling reaction that must be controlled at a low level. Relatively low levels of 4-ADPA result in unacceptably low yields for the coupling reaction and severe poisoning of the hydrogenation catalyst. It is surprising that such small amounts of an aromatic amine similar to aniline would have such severe consequences. A good control level for 4-ADPA in recycle base plus recycle aniline is such that in the coupling reactor, the molar ratio of 4-ADPA/nitrobenzene is less than about 0.05, preferably less than about 0.03 and most preferably less than about 0.015. Methanol exacerbates the effect of 4-ADPA and results in formation of formaldehyde, which is a catalyst poison. An acceptable level of methanol in the process has not been established, but is best to get the level as low as possible. Hydrogenation catalyst may also be a deleterious impurity when contained in recycle base, so it is best to get the level as low as possible.

It is to be understood that recycling of the base-containing aqueous phase may, but does not need to, take place simultaneously with recycling of the hydrogenation catalyst. More in particular, depending upon the plant design, the aqueous phase and the hydrogenation catalyst which result from one process cycle may end up in different subsequent cycles. Furthermore, it is normal to collect recycle base in a holding tank, so that batch identity is completely lost.

In one preferred embodiment of the invention process, the hydrogenation catalyst, after its separation from the hydrogenation reaction mixture, is washed with water and the washed catalyst is reused to form a subsequent step (ii) reaction mixture. A typical catalyst wash comprises repeatedly, say, up to four times, washing the catalyst with about 50 to about 500 liter of water (typically demineralized) per 1.0 kg of catalyst (dry basis). It is a special feature of the invention process that in this manner catalyst activity can be maintained at a high level and that batch-to-batch variability is kept at a sustainable minimum. It is speculated that adherence to the water to base ratios and the minimum recycle of 4-ADPA and methanol to the step (i) reaction in accordance with the invention process prevents the formation—even after repeated cycles—of poisons which cannot be removed from the hydrogenation catalyst by such an attractively simple measure as washing with water.

In another preferred embodiment of the invention process, the hydrogenation catalyst, after its separation from the hydrogenation reaction mixture, is kept as a slurry in water. It has been found that keeping the catalyst in aqueous slurry between cycles is also beneficial to keeping the catalyst activity at desirably high levels and minimizing batch-to-batch variability. In such slurries, which can be kept in constant motion, for example by stirring and/or by pumping through a recirculation line, the solid to liquid ratio can vary within wide limits, but in general this ratio is in the range of about 0.01 to about 0.25, preferably within the range of about 0.02 to about 0.15. When the catalyst is to be reused, this can be done by adding it to the hydrogenation reactor in the form of the slurry in which it was kept. Evidently, it is also possible to dewater the slurry to a higher solids content slurry or even to a paste before addition of the catalyst to the hydrogenation reactor.

The process steps of the present invention for the preparation of 4-aminodiphenylamines may be conducted as batch processes or they may be performed continuously using means and equipment well known to the skilled person.

Other features of the process include the recovery of aniline if aniline is used in a molar excess relative to the nitrobenzene. In this embodiment, when the 4-aminodiphenylamine is isolated from the organic phase, typically by distillation, aniline is recovered in the same distilling operation and it is then passed to a holding tank from which it can be reused to form a subsequent step (i) reaction mixture. The best approach would be to employ a series of distillation columns for recovering aniline and purifying the 4-ADPA.

A further embodiment of the invention process addresses the problem of the formation, during the reaction between aniline and nitrobenzene, of unwanted by-products, in particular azobenzene and/or azoxybenzene. Depending on the step (i) reaction conditions, these compounds are formed in amounts ranging from about 1% to about 25%, based on the limiting reagent which typically is nitrobenzene. In the invention process any such products pass to the step (ii) hydrogenation reactor whereby azobenzene and azoxybenzene may be converted to hydrazobenzene and possibly some aniline. Since hydrazobenzene will thermally degrade in the distillation system to impurities, formation of hydrazobenzene herein should preferably, but not necessarily, be minimized. Some azobenzene and/or azoxybenzene can also form in the step (ii) hydrogenation from unreacted nitrobenzene left in the step (i) reaction mixture.

It has been found that azobenzene and/or azoxybenzene formed during the coupling and/or hydrogenation reactions can be converted to aniline by catalytic hydrogenation, without formation of the hazardous compound benzidine. It is known in the literature that a high concentration of acid promotes the catalytic hydrogenation of azobenzene to hydrazobenzene to aniline, but that acid also promotes rearrangement of hydrazobenzene to benzidine. However, the use of catalytic amounts of acid have not been reported for hydrogenation of azobenzene to aniline During working-up of the organic phase after the hydrogenation reaction, azobenzene and azoxybenzene are distilled-off and passed to a separate reactor in which they are subjected to a hydrogenation in the presence of a precious metal catalyst with a co-catalyst comprising a weak acid, weak base or pH neutral component to form aniline. Suitable catalysts are the same as catalysts used in step (ii) hydrogenation. The co-catalyst, which may suitably be a weak organic acid, such as acetic acid, stearic acid, octanoic acid and/or an acidic carbon, such as a commercially available activated carbon, preferably with bound acidity, will promote aniline formation without benzidine formation. The weak acid or weak base or pH neutral co-catalyst can be introduced together with the hydrogenation catalyst and/or as part of the hydrogenation catalyst. An example of the latter would be an acidic carbon support, preferably with bound acidity, for a hydrogenation catalyst such as platinum or palladium on carbon. Aniline can be used as a solvent, where the amount is not critical, and/or as a convenient medium for handling recycle catalyst as a slurry. The process conditions may be temperature from about 70° to about 250° C. and pressure from about 1 to about 25 barg. Suitable reactors are the same as described above for the step (ii) hydrogenation. After removal of the catalyst and co-catalyst, the aniline is recovered by distillation. Phenazine, any phenazine-N-oxide and any other impurities which are distilled off with the azobenzene and azoxybenzene from hydrogenation step (ii) have very high boiling points, as do any of the hydrogenation products of the impurities. Therefore, they will not be recycled, since they will not distill off with the aniline following the hydrogenation with co-catalyst step in which the aniline is formed. The so recovered aniline can then be used to form part of the step (i) reaction mixture.

It has been found that a hydrogenation catalyst and acidic carbon co-catalyst may effectively be re-used or recycled for hydrogenation of azobenzene and/or azoxybenzene to aniline in subsequent batches of azobenzene and/or azoxybenzene containing streams with minimal increase in reaction time.

The present invention further relates to a process for preparing alkylated derivatives of optionally substituted 4-aminodiphenylamines, in particular for preparing alkyl derivatives of 4-ADPA itself, which are useful for the protection of rubber products, in which process an optionally substituted aniline and an optionally substituted nitrobenzene are coupled and subsequently hydrogenated according to the invention process, after which the 4-aminodiphenylamine so obtained is reductively alkylated to an alkylated derivative of 4-aminodiphenylamine according to methods known to the person skilled in this technical field. Typically, the 4-ADPA and a suitable ketone or aldehyde are reacted in the presence of hydrogen and a catalyst, such as copper chromite, platinum-on-carbon or palladium-on-carbon. Suitable ketones include acetone, methylisobutyl ketone, methylisoamyl ketone, and 2-octanone. See for example U.S. Pat. No. 4,463,191, and Banerjee et al, *J. Chem. Soc. Chem. Comm.* 18, 1275–1276 (1988). Other suitable catalysts can be the same as, but not limited to, those described above for the step (ii) hydrogenation.

The invention is illustrated by the following examples.

Typical Lab Preparation Procedure

Typical procedures according to the invention for coupling and hydrogenation reactions are described below. Any variations from the mole ratios and operating conditions of these procedures are noted in the examples. These variations are within the scope of the invention, except when used for comparison. Actual charges varied with equipment size and some reactions had a heel from the previous reaction batch at the start.

1242 g of 25 wt. % aqueous tetramethylammonium hydroxide solution (TMAH) was concentrated to about 35 wt. %, at a pressure in the range of 70 mbara and with temperature rising from about 40° C. to about 60° C. Then 1547 g of aniline was added and water removal was continued by distillation of the water-aniline azeotrope, at about 90 mbara and with temperature rising from about 50° C. to about 80° C., until a final water/TMAH molar ratio of 4.0–6.0 was obtained. Within 2 hours, 382 g of nitrobenzene was added while distillation of the aniline/water azeotrope was continued, at about 90 mbara and about 80° C., in order to maintain the right water/TMAH ratio in the reaction mixture. The coupling batch was held with agitation for 10 to 25 minutes after completion of the nitrobenzene feed. Distillation rate was tuned to reach a water/TMAH molar ratio of 1.0–2.5 at the end of the reaction (i.e. nitrobenzene feed plus hold time). Water was added to the finished coupling reaction mass for dilution (total water/TMAH molar ratios of 9–15) together with a small quantity of commercially available 3% Pd/C catalyst. Then the mixture was hydrogenated at 80–90° C. and a hydrogen pressure of 8 bara. The hydrogenation reaction was stopped when hydrogen uptake reached prescribed minimum values. The quantity of catalyst intake was tuned to meet hydrogenation times of less than 1.5 hour. Data from HPLC analysis of Intermediate and final products were used to calculate unreacted nitrobenzene (i.e. the percent of nitrobenzene charge remaining in the batch at the end) and nitrobenzene selectivity (i.e. (moles of NODPA+NDPA)$_{formed}$/(moles of nitrobenzene)$_{converted}$).

EXAMPLE 1

This example illustrates the excellent hydrogenation results (reaction time and catalyst intake) that are obtained when the coupling reaction is performed according to the invention. Results are decidedly superior to those demonstrated in U.S. Pat. No. 5,739,403.

The coupling reaction was carried out as described in the typical procedure. Fresh (pure) raw materials were used as feed. Water/TMAH molar ratio decreased from 4.8 at the start to 1.6 at the end of nitrobenzene addition. The total time for nitrobenzene addition plus hold was 130 minutes. Nitrobenzene selectivity was 94.0% with 0.4% unreacted nitrobenzene. Another coupling reaction carried out in a similar manner gave nitrobenzene selectivity of 95.1% with 0.1% unreacted nitrobenzene. Dilution water was added to the first coupling batch above (total water/TMAH ratio of 11.2) and the reaction mixture was hydrogenated using the 3% Pd/C catalyst. Catalyst intake was 0.17 mg atoms of Pd per mole of nitro/nitroso compounds and hydrogenation time was 33 minutes. By comparison, coupling reaction mass in the working examples of U.S. Pat. No. 5,739,403, that were diluted to water/TMAH molar ratios above 10, required a much higher catalyst intake (1.21 mg atoms Pt per mole of nitro/nitroso compounds) for a much greater reaction time (4 hours).

EXAMPLE 2

This example illustrates the harmful effect on the coupling and hydrogenation reactions from the presence of 4-ADPA during the coupling reaction. Results clearly show the large negative effect on selectivity of the coupling reaction and activity in the hydrogenation reaction. This illustrates that 4-ADPA must be controlled at a low level in process recycle streams.

The Example 1 coupling reaction was repeated twice, starting with fresh 25 wt. % aqueous TMAH solution and two different samples of recycle aniline, that were obtained after a large number of full recycle trials. The first coupling reaction used recycle aniline containing 3.9 wt. % 4-ADPA and fresh TMAH solution. Water/TMAH molar ratio decreased from 5.5 at the start to 1.2 at the end of nitrobenzene addition. Nitrobenzene selectivity was only 82.7% with 0.3% unreacted nitrobenzene. Dilution water was added to this coupling batch (total water/TMAH molar ratio of 11.2) and the mixture was hydrogenated using the 3% Pd/C catalyst. Catalyst intake was 0.17 mg atoms of Pd per mole of nitro/nitroso compounds. After 60 minutes of hydrogenation time, conversion was only 35%. For comparison, a second coupling reaction used recycle aniline with 0.0% 4-ADPA and fresh TMAH solution. Water/TMAH ratio decreased from 5.1 at the start to 1.6 at the end of nitrobenzene addition. Nitrobenzene selectivity was significantly higher at 96.2% with 3.5% of the nitrobenzene unreacted. This second coupling batch, with similar dilution by water and the same catalyst intake, was completely hydrogenated in 46 minutes.

EXAMPLE 3A

This example illustrates that there can be a loss of reactivity with recycle TMAH solution vs fresh TMAH solution for the coupling and hydrogenation reactions. The impact is especially great on catalyst activity for hydrogenation, because of impurities that are formed during the coupling and hydrogenation reactions from impurities contained in the recycle base solution. The effect on nitrobenzene selectivity is variable, which is explained by a variable level of impurities in the recycle TMAH solution. Such impurities include 4-ADPA and impurities resulting from the decomposition of TMAH, which may include methanol, methoxide, formaldehyde, formic acid and tetramethylammonium carbonate. Operation according to this invention will minimize the harmful impurities formed and will thus minimize these negative effects of reusing the aqueous phase which contains the base.

The Example 1 coupling reaction was repeated twice, starting with fresh aniline and two different samples of 19–25 wt. % aqueous TMAH solution, that were obtained after a large number of full recycle trials. For the first batch, water/TMAH molar ratio decreased from 5.1 at the start to 2.2 at the end of nitrobenzene addition. Nitrobenzene selectivity was 93.7% with 1.9% unreacted nitrobenzene. For the second batch, water/TMAH molar ratio decreased from 5.4 at the start to 2.2 at the end of nitrobenzene addition. Nitrobenzene selectivity was 89.3% with 4.7% unreacted nitrobenzene. Dilution water was added to each of the coupling batches (total water/TMAH molar ratio of 11.2) and the reaction mixtures were hydrogenated using the 3% Pd/C catalyst. Catalyst intake was 0.17 mg atoms of Pd per mole of nitro/nitroso compounds for each reaction. Conversions for the two hydrogenations, after 60 minutes of reaction time, were only 70% and 48% respectively, much worse than for Example 1 with fresh base.

EXAMPLE 3B

Another hydrogenation was carried out with the first coupling batch material from Example 3A. An increased quantity of catalyst was used to reach the same hydrogenation activity level as obtained in Example 1. With a catalyst intake of 0.50 mg atoms of Pd per mole of nitro/nitroso compounds, hydrogenation time was 30 minutes.

Although larger quantities of catalyst are required to reach an activity level for hydrogenation times of ±30 minutes, catalyst intake is still low compared to data reported in U.S. Pat. No. 5,739,403 (for a 4 hour reaction time). This illustrates that recycle of TMAH solution may be employed by proper implementation of this process. It is expected that catalyst intake with recycle base will be lower than shown here as experience is gained with operation of this process on a commercial scale. It is also expected that catalyst intake will be even lower when a relatively large recycle catalyst mass is used.

EXAMPLE 3C

This example demonstrates that the impurities in recycle base are themselves not significant catalyst poisons. Coupling reaction product as prepared in Example 1 was diluted with either a 35 wt. % aqueous fresh based solution or a 35 wt. % aqueous recycle base solution and a small amount of water. The dilution factor was 0.75 parts base solution per 1.0 part of coupling mass. The total water/TMAH molar ratio was 24.3 after dilution. This mixture was hydrogenated using the 3% Pd/C catalyst. Catalyst intake was 0.28 mg atoms of Pd per mole of nitro/nitroso compounds. Reaction times were 29 minutes for fresh base and 47 minutes for recycle base.

These results show only a small negative effect of recycle base compared with fresh base on hydrogenation catalyst activity. Therefore, the much larger negative effects on hydrogenation catalyst activity obtained when recycle base is used for coupling reactions, as in Example 3A, must come from catalyst poisons generated from recycle base impurities during the coupling reaction. It is further possible that some additional new impurities that were made in the coupling reactor could generate additional catalyst poisons in the hydrogenation reactor.

EXAMPLE 4

This example shows that the effect of impurities in recycle streams can be synergistic. When recycle aniline containing 4-ADPA is used together with recycle base, the negative effects on coupling and hydrogenation reactions are worse than when either recycle material is used alone. The results are lower nitrobenzene selectivity and significantly lower catalyst activity. This further illustrates that TMAH decomposition must be minimized and that 4-ADPA and other impurities must be controlled at a low level in recycle streams, by operation according to this process.

The Example 1 coupling reaction was repeated using recycle aniline containing 3.9 wt. % 4-ADPA and recycle TMAH solution. Water/TMAH ratio decreased from 5.5 at the start to 1.9 at the end of nitrobenzene addition. Nitrobenzene selectivity was only, 81.6% with 2.0% of the nitrobenzene unreacted. Dilution water was added to the coupling batch (total water/TMAH ratio of 11.2) and the reaction mixture was hydrogenated using the 3% Pd/C catalyst. Catalyst intake was 0.17 mg atoms of Pd per mole of nitro/nitroso compounds. After 60 minutes of hydrogenation time, conversion was <10%.

EXAMPLE 5

This example illustrates the harmful and synergistic effect of some specifically identified process impurities on selectivity of the coupling reaction and thus emphasizes the need to minimize these impurities by the process of this invention. It also illustrates how methanol (a TMAH decomposition product) can be converted to the catalyst poison formaldehyde. Various impurities, alone and in combination, were spiked into lab coupling reactions that were made according to the typical procedure with fresh raw materials. The reactions were held for 30 minutes after the end of nitrobenzene feed, while continuing to distill out water and aniline, and then analyzed by HPLC. The impurity levels used in Table 1 are 0.9 wt. % for 4-ADPA, 0.015 wt. % for Pd and 2.3 wt. % for methanol (each as wt. % of the total raw material charge). These are higher levels than normal for this process in order to demonstrate an unambiguously significant effect. Although lower impurity levels will exhibit effects of smaller magnitude, the effects are expected to be cumulative with recycling of base and aniline. For these tests, the impurities were spiked at various times during a coupling reaction batch. Catalyst was added at the start with the base, 4-ADPA was added with the aniline and methanol was added in three portions to allow for volatility losses, i.e. at the start, with aniline and with nitrobenzene. It is also known that methanol will react to methoxide at dry, high pH conditions such as exist in the coupling reactor.

The results in Table 1 show that 4-ADPA alone and in combination with catalyst, methanol, or both, causes significant loss of nitrobenzene selectivity for the coupling reaction. Note that the worst case by far was when catalyst was combined with 4-ADPA and methanol. These results also indicate that methanol is reactive in the coupling reactor in the presence of 4-ADPA. It is most likely that methanol and/or methoxide are acting as reducing agents, since such chemistry is known in the literature to occur at conditions such as those in the coupling reactor. Methanol and/or methoxide would in turn be oxidized to the catalyst poison formaldehyde. It is important to note that methanol does not reduce selectivity without 4-ADPA. However, other impurities could also interact to cause oxidation of methanol and/or methoxide to formaldehyde in the coupling reactor. Furthermore, it is known in the literature that alcohols and alkoxides in the presence of a catalyst can reduce nitro and nitroso compounds to amines, specifically for 4-ADPA from 4-nitrodiphenylamine. With methanol and/or methoxide, this would also result in formation of formaldehyde. So methanol and/or methoxide can also be oxidized to formaldehyde in the hydrogenation reactor, when they are in contact with 4-NDPA and a relatively large amount of catalyst. Finally, these are not presumed to be the only impurities that can cause harmful effects on the coupling and hydrogenation reactions.

TABLE 1

| Coupling Reaction Impurities | Selectivity (%) |
|---|---|
| None | 92.8 |
| Pd/C | 95.6 |
| Methanol | 93.2 |
| Pd/C + Methanol | 92.0 |
| 4-ADPA | 86.7 |
| 4-ADPA + Pd/C | 85.8 |
| 4-ADPA + Methanol | 82.5 |
| 4-ADPA + Pd/C + Methanol | 62.7 |

EXAMPLE 6

This example illustrates the benefits of reduced TMAH decomposition from performing the coupling reaction (nitrobenzene feed plus hold) at or above a water/TMAH molar ratio of 0.6 according to this invention. Three lab coupling reactions were made according to the typical procedure at ~76 mbara, with molar ratios of aniline/nitrobenzene=6.0 and TMAH/nitrobenzene=1.05. Water/TMAH molar ratios at the end of both nitrobenzene feed and the hold were variable. Nitrobenzene feed time varied from 2 to 3 hours. All batches had a 4 hour hold at 75° C., during which time distillation of the water/aniline azeotrope was continued, as prescribed in U.S. Pat. No. 5,739,403. TMAH in the reaction mass after nitrobenzene feed and after the hold was determined by titration analysis of reaction mass samples. TMAH decomposition was determined by difference from the starting amount of TMAH. For comparison, another coupling reaction batch, made by the typical procedure according to this invention, was held for 2 hours at 80° C. at a constant water/TMAH molar ratio.

Table 2 shows that TMAH decomposition increases as the water/TMAH molar ratio at the end of nitrobenzene feed decreases. The results also show the disastrous effect of the 4 hour hold with continued distillation that is taught by U.S. Pat. No. 5,739,403, wherein decomposition rates were 0.5–1.8% per hour, because the water/TMAH ratio drops below the minimum of 0.6 specified by this invention. By contrast, TMAH decomposition was only 0.15% per hour during a 2 hour hold (at 5° C. higher temperature) when the water/TMAH ratio was kept at 1.4, above the minimum for this invention. So operation in accordance with this invention, to keep the water/TMAH molar ratio at or above 0.6, will minimize decomposition of TMAH during nitrobenzene feed plus hold time. Such operation will also minimize formation of catalyst poisons derived from impurities related to TMAH decomposition. By comparison, operation according to U.S. Pat. No. 5,739,403 will give unacceptable TMAH decomposition. The resultant formation of high levels of catalyst poisons explains why U.S. Pat. No. 5,739,403 hydrogenations took 4 hours, even with a very high catalyst intake. Actual TMAH decomposition that can be achieved commercially, with optimized operation according to this invention, can be expected to be lower than in Table 2. For example, ~1% decomposition of TMAH has been demonstrated for coupling reactions carried out according to this invention, with nitrobenzene feed plus hold times less than 3.5 hours.

TABLE 2

| Nitrobenzene | Water/TMAH Molar Ratio | | Total TMAH Decomposition % of Initial TMAH | |
|---|---|---|---|---|
| Feed Time Hours | End of NB Feed | End of 4 h Hold Period | End of NB Feed | End of 4 h Hold Period |
| 2.0 | 0.93 | 0.26 | 2.43 | 9.64 |
| 2.5 | 1.33 | 0.40 | 2.13 | 4.08 |
| 3.0 | 0.77 | 0.17 | 3.35 | 7.85 |

EXAMPLE 7

This example further illustrates the importance of carrying out the coupling and hydrogenation reactions above a minimum water/TMAH molar ratio for minimum TMAH decomposition. Two samples of aniline, TMAH and water mixtures, with water/TMAH molar ratios of 5.0 and 2.7, were placed in separate sealed vials. The mixtures were 0.6 g aniline with either 0.2 g of water plus TMAH for ratio=5 or 0.16 g of water plus TMAH for ratio=2.7. The two vials were held in an oven for 2 hours at 80° C., which is in the specified temperature range of this invention for both the coupling and hydrogenation reactors. After removal from the oven, the amount of trimethylamine formed from decomposition of TMAH was determined for each sample by GC analysis of the headspace. The results indicated that TMAH decomposition was 0.2% for water/TMAH molar ratio of 5 and 2.0% for water/TMAH molar ratio of 2.7. Therefore, TMAH decomposition increases as the amount of water is reduced. Lower water/TMAH molar ratios than were tested here are acceptable at the end of the coupling reaction, because most of the TMAH has been converted to the more stable salts of 4-nitrosodiphenylamine and 4-nitrodiphenylamine. However, all of the TMAH is present at the beginning of the coupling reaction and at the end of hydrogenation, when all of the TMAH has been regenerated. Therefore a higher water/TMAH molar ratio is needed to minimize TMAH decomposition at the start of the coupling reaction and during hydrogenation.

EXAMPLE 8

This example demonstrates the effect on hydrogenation of various impurities resulting from decomposition of TMAH. Coupling reaction product as prepared in Example 1 was 'spiked' respectively with methanol (0.9 wt. %), formaldehyde (0.9 wt. %), formic acid (1.8 wt. %) or TMA-carbonate (3.8 wt. %) and hydrogenated. Catalyst intake was 0.17 mg atoms of Pd per mole of nitro/nitroso compounds. Reaction times in Table 3 show a large negative effect of formaldehyde addition on hydrogenation activity, indicating that formaldehyde is a catalyst poison. This illustrates that TMAH decomposition must be kept to a minimum by operation according to this process.

TABLE 3

| Impurity Spiking | | Reaction Time |
|---|---|---|
| | (wt. %) | (min) |
| None | — | 33 |
| Methanol | 0.9 | 32 |
| Formaldehyde | 0.9 | >>60[*] |
| Formic acid | 1.8 | 54 |
| TMA-carbonate | 3.8 | 37 |

[*]Initial hydrogenation rate was only 4% of Example 1

EXAMPLE 9A

This example illustrates that fresh catalyst intake can be reduced by pretreatment of the hydrogenation feed with low activity recycle catalyst. The Example 1 coupling reaction was repeated using a 25 wt. % aqueous TMAH solution and '4-ADPA contaminated' aniline, both obtained after a large number of full recycle trials. The coupling reaction mixture was diluted to a water/TMAH molar ratio of ~9 and then hydrogenated at 90° C. and 8 bara hydrogen pressure, using 3% Pd/C (% based on dry weight of metal plus carbon) as catalyst. Based on a study of reaction time vs fresh catalyst intake with this coupling reaction mixture, a catalyst intake of 0.63 mg atoms of Pd per mole of nitro/nitroso compounds would be needed to get a hydrogenation time of 82 minutes. By comparison with Example 3B, this coupling reaction mixture had a relatively high level of catalyst poisons. A new sample of the same coupling reaction mixture was pretreated for 15 minutes at 90° C. under hydrogen pressure of 8 bara with about 1 wt. % of a Pd/C catalyst wet filter cake (~25 wt. % solids) with low residual activity, that was obtained after a large number of full recycle trials. Although there was some hydrogen uptake, initial activity was only 2–4% of that observed in Example 1. This catalyst was removed by filtration, fresh catalyst was added and the treated reaction mixture was hydrogenated at the same conditions as above. With a lower catalyst intake of 0.28 mg atoms of Pd per mole of nitro/nitroso compounds, reaction time was again 82 minutes. It can be expected that an even larger improvement would be obtained by pretreatment with recycle catalyst of higher residual activity.

EXAMPLE 9B

This example illustrates the beneficial effect of using fresh catalyst together with a mass of recycle catalyst that has low residual activity. The coupling reaction mixture and recycle catalyst were the same as those used in Example 9A. Coupling reaction mixtures were diluted to a water/TMAH molar ratio of about 9 and then hydrogenated at 90° C. and 8 bara of hydrogen pressure, using two different ratios of fresh 3% Pd/C catalyst intake to recycle Pd/C catalyst mass. The recycle catalyst was in the form of a wet filter cake, estimated to contain 25 wt. % solids. The actual solids content could not be determined accurately because of organic compounds adsorbed on the recycle catalyst. The first hydrogenation batch, with a fresh catalyst intake of 0.29 mg atoms Pd/mole nitro/nitroso compounds and a recycle catalyst solids to fresh catalyst solids weight ratio of about 2.5, had a hydrogenation time of 96 minutes. Based on the above study of reaction time vs catalyst intake with the same coupling reaction mixture, a fresh catalyst intake of about 0.59 mg atoms Pd/mole nitro/nitroso compounds would be needed without any recycle catalyst to obtain the same hydrogenation time of 96 minutes. The second hydrogenation batch, with a smaller fresh catalyst intake of 0.115 mg atoms Pd/mole nitro/nitroso compounds and a higher recycle catalyst solids to fresh catalyst solids weight ratio of about 18, had a shorter hydrogenation time of 57 minutes. In this case, a fresh catalyst intake of about 0.74 mg atoms Pd/mole nitro/nitroso compounds would be needed without recycle catalyst to obtain the same hydrogenation time of 57 minutes.

These results were achieved with a recycle catalyst mass of very low residual activity, as evidenced by the low initial activity of 2–4% when only recycle catalyst was used, and a coupling reaction mixture with a relatively high level of catalyst poisons. It can be expected that good results will be achieved at even lower weight ratios when recycle catalyst mass of higher residual activity is used with coupling reaction mixtures containing lower levels of catalyst poisons.

EXAMPLE 10

This example illustrates the efficacy of various catalysts for hydrogenation of coupling reaction material prepared according to the invention. A coupling reaction was prepared in a 250 L pilot scale reactor with all fresh raw materials, following the typical procedure above. The water/TMAH molar ratio decreased from 4.7 at the start to 1.6 at the end of reaction. Portions of the coupling reaction mass were hydrogenated following the typical procedure of the invention, with various catalysts. The molar ratio of water/TMAH was 9.4 in the hydrogenation reactor for the examples according to the invention, which is just below the lower limit of water/TMAH ~10 that is claimed in U.S. Pat. No. 5,739,403

The results in Table 4 indicate that various catalysts can be used efficiently for hydrogenation of coupling reaction material made according to the invention. The comparison with U.S. Pat. No. 5,739,403 clearly shows the advantage of performing coupling and hydrogenation reactions with water/TMAH molar ratios maintained above the minimums in accordance with this invention. Furthermore, the greatly superior catalyst intakes and hydrogenation reaction times were achieved with less water than specified by U.S. Pat. No. 5,739,403. This indicates that the amount of water is not the most important parameter for good hydrogenation performance (as claimed in U.S. Pat. No. 5,739,403), but rather proper control of the water/base molar ratios for the coupling and hydrogenation reactions according to this invention.

TABLE 4

| Catalyst Type | Catalyst Intake mg atoms metal/mole | Reaction Time Minutes |
|---|---|---|
| Examples according to this invention | | |
| 3% Pd/C | 0.154 | 31 |
| 5% Pd/C | 0.154 | 20 |
| 1% Pt/C | 0.084 | 12 |
| 5% Pt/C | 0.084 | 13 |
| 5% Rh/C | 0.159 | 25 |
| Example 1 of U.S. Pat. No. 5,739,403 (not according to this invention) | | |
| 5% Pt/C | 1.21 | 240 |

EXAMPLE 11

This example illustrates the effect of water/TMAH molar ratio in the hydrogenation batch on recycle catalyst activity. Ten lab coupling reactions were carried out according to the typical procedure of this invention and blended. The final water content of the blend was water/TMAH=1.5 molar ratio. Portions of the blend were diluted with various amounts of water and then hydrogenated at 85–90° C. and about 8 bara hydrogen pressure. The first cycle at each water level was carried out with fresh 3% Pd/C catalyst at a charge of about 0.19 mg atoms Pd/mole of nitro/nitroso compounds. Cycles 2 and 3 used catalyst recycled from the previous batch.

Table 5 shows that above a water/TMAH molar ratio of 5, increasing the amount of water had no significant effect on reaction time for the first cycles with fresh catalyst. When catalyst was recycled, however, there was a clear effect of water/TMAH molar ratio on reaction time. This shows that increasing the water level increased the retention of activity by the catalyst when it was recycled, so water reduced the impact on catalyst from poisons generated in the process.

Therefore, addition of water will reduce fresh catalyst intake (with or without use of recycle catalyst) that is needed to produce a constant hydrogenation time. This further indicates that with coupling and hydrogenation reactions carried out according to this invention, good hydrogenation conversions and reaction times can be obtained with water/TMAH ratios well below 10 (which is the lower end of the range claimed by U.S. Pat. No. 5,739,403). Furthermore, U.S. Pat. No. 5,739,403 demonstrates a long reaction time of 4 hours with a large fresh catalyst intake of about 1.21 mg atoms Pt/mole nitro/nitroso compounds at all water levels within the range claimed in U.S. Pat. No. 5,739,403. Such a long reaction time with a high catalyst intake shows that the U.S. Pat. No. 5,739,403 coupling reaction product contained significantly more catalyst poisons than coupling reaction product made according to this invention. Finally, Cycle 1 results in Table 5 indicate that with such a high catalyst intake as in U.S. Pat. No. 5,739,403, coupling reaction product made according to this invention would be completely hydrogenated within 4 hours at water/TMAH molar ratios well below 4.7 and even at water/TMAH molar ratio of 4.

TABLE 5

| Cycle No. | Time Minutes | Water/TMAH Molar Ratio |||||| 
|---|---|---|---|---|---|---|---|
| | | 1.5 | 4.7 | 6.2 | 7.8 | 11.0 | 14.1 |
| | | Conversion of Nitro/Nitroso Compounds (%) |||||| 
| 1 | 25 | 24.8 | 76.5 | 98.7 | 100.0 | >98 | 97.6 |
| 2 | 85 | <11.0 | 20.6 | 53.1 | 63.9 | 88.0 | 94.5 |
| 3 | 135 | 13.5 | 13.2 | 28.9 | 36.5 | 61.1 | 72.5 |

EXAMPLE 12

This example further illustrates the effect of water in the hydrogenation batch on recycle catalyst activity. Three coupling reaction batches were prepared according to the typical procedure in a 22 L lab reactor at ~27 mbara pressure. Molar ratios used were aniline/nitrobenzene=4.8–6.0 and TMAH/nitrobenzene=1.05, with reaction ending at water/TMAH=1.2–1.5. Hydrogenations were then done at 80° C. and about 17.7 bara with a variable amount of water in the batch. Catalyst was recycled ten times at each water level, with fresh catalyst added as needed to achieve a reasonably consistent reaction time. In order to adjust for the variations that inevitably did occur for reaction time, catalyst usage is expressed as total mg atoms of Pd used per total moles of nitro/nitroso compounds reduced per hour over the eleven batch series.

Results in Table 6 show that Cycle 1 reaction time (and hence initial catalyst activity) was not affected by the amount of water in the batch, whereas catalyst usage decreased with increasing amount of water added. Therefore, retention of activity by recycle catalyst was improved by adding more water. It is especially significant that even though the lowest water level also had the lowest initial fresh catalyst intake, there was still enough catalyst activity for a normal hydrogenation reaction time, because coupling reaction material was made according to this invention. As in other examples, these Cycle 1 reaction times contrast greatly with the results reported in U.S. Pat. No. 5,739,403 with fresh catalyst, i.e. 4 hour reaction time with 1.21 mg atoms Pt per mole of nitro/nitroso compounds.

TABLE 6

| Molar Ratio in Hydrogenation Batch Water/TMAH | Cycle 1 Fresh Catalyst Intake mg atoms Pd/mole | Cycle 1 Reaction Time Minutes | Catalyst Usage After 11 Cycles mg atoms Pd/mole/h |
|---|---|---|---|
| 11.1 | 0.32 | 42 | 0.076 |
| 15.6 | 0.49 | 41 | 0.048 |
| 22.5 | 0.49 | 44 | 0.039 |

EXAMPLE 13

This example demonstrates the beneficial effect on activity of recycled catalyst from washing catalyst with water, after it has been separated from hydrogenation mass. Coupling reaction material, prepared in a lab reactor by the typical procedure according to this invention, was hydrogenated at 85–90° C. and about 8 bara with a water/TMAH molar ratio of about 8.7. Three series of hydrogenation batches of three cycles each were prepared in this manner, with a fresh catalyst intake of about 0.2 mg atoms Pd/mole of nitro/nitroso compounds to the first cycle. Catalyst was recycled for the second and third cycles of each series, without fresh catalyst addition. For one series the catalyst was washed with deionized water at 60–70° C. under about 4.5 bara of hydrogen pressure, once between Cycles 1 and 2 and once again between Cycles 2 and 3. The wash ratio was 500 ml of water per g of catalyst. Washing was performed by adding the water to the lab autoclave, agitating for 5 minutes and then filtering off the water through the internal filter. For the two baseline series, the catalyst was held in the autoclave under residual hydrogen pressure between batches.

Results in Table 7 show that water washing gives a small improvement in hydrogenation rate compared to the baseline cases, which did not have the water wash. The magnitude of the improvement was slightly higher for the third cycle than for the second cycle. This again illustrates the ability of water to remove catalyst poisons generated in the process operated according to the invention. It can be expected that water washing will have an even greater effect at lower water/TMAH molar ratios. As in other examples, these Cycle 1 reaction times contrast greatly with the results reported in U.S. Pat. No. 5,739,403 with fresh catalyst, i.e. 4 hour reaction time with 1.21 mg atoms Pt per mole of nitro/nitroso compounds.

TABLE 7

| Cycle No. | Time minutes | Baseline | Water/TMAH Molar Ratio = 8.7 Water Wash Conversion (%) | Baseline |
|---|---|---|---|---|
| 1 | 37–38 | 100.0 | 100.0 | 100.0 |
| 2 | 90 | 78.0 | 91.8 | 77.1 |
| 3 | 120 | 58.5 | 75.4 | 50.3 |

EXAMPLE 14

This example demonstrates that keeping catalyst in contact with water as a slurry between batches is equivalent to water washing with a relatively small amount of water. Coupling reaction material was prepared in a 100 gallon pilot plant reactor according to the typical procedure at 69–100 mbara. Molar ratios were aniline/nitrobenzene=4.8 and TMAH/nitrobenzene=1.05. Portions of the coupling batch were hydrogenated in a lab reactor at 80° C. and about 8.6 bara with a water/TMAH molar ratio of about 15 and a 3% Pd/C catalyst. In the middle of a catalyst recycle series, a comparison was made between water washing and simply holding the catalyst mass in contact with the water as a slurry. Washing was performed by adding water to the catalyst remaining in the autoclave, after removal of the previous batch through the internal filter. The slurry was agitated for 10–15 minutes at 80° C. with 14.8 bara of hydrogen pressure and then the water was removed through the filter. For the case where water was left with the catalyst, the water was added to the catalyst in the autoclave after removal of the previous batch through the internal filter. The water and catalyst were then held under residual hydrogen pressure until start of the next batch. The quantity of water left with the catalyst was subtracted from the quantity of water normally added for hydrogenation, so that the total water in the hydrogenation reactor was the same for both cases.

Results in Table 8 indicate that the water wash and water slurry contact had a comparable effect on reaction time. Prior to this comparison study, the catalyst mass activity had stabilized at reaction times of 53–57 minutes. Washing at this point with no fresh catalyst intake and using 263 ml water per g of catalyst mass, gave reaction time increases of 4, 7, 5 and 16 minutes over four cycles. In a comparable catalyst recycle series after stabilization, two cycles with no fresh catalyst intake and no water wash had reaction time increases of 5 and 15 minutes. (The greater increase for the second cycle without wash vs the second cycle with wash is further evidence of a small improvement from water washing.) For this example the reaction time was allowed to increase above the stabilized times in order to magnify any effects, so that any differences would be easier to detect. Therefore, in this study with a smaller water wash and less active catalyst mass, the larger increase in reaction time was expected. Since the increase was the same for water washing vs merely maintaining contact with water, the procedures were equivalent.

TABLE 8

| Description of Experiment | Catalyst Mass g | Water/Catalyst (ml/g) Wash | Water/Catalyst (ml/g) Slurry | Reaction Time Minutes |
|---|---|---|---|---|
| Base Case | 1.76 | 57 | 0 | 89 |
| Slurry Effect | 1.76 | 0 | 57 | 107 |
| Base Case | 1.86 | 54 | 0 | 88 |
| Wash Effect | 1.86 | 54 | 0 | 107 |

EXAMPLE 15

This example illustrates that an acidic carbon, such as a commercially available activated carbon, is an effective co-catalyst for hydrogenation of azobenzene to aniline, with high yield and low catalyst usage without formation of benzidine. The suitability of the recovered aniline for recycle to the coupling reactor is also demonstrated.

It is known in the literature that highly basic conditions, such as are found in the step (ii) hydrogenation reactor, strongly inhibit hydrogenation of azobenzene to aniline (hydrogenation stops at formation of hydrazobenzene). It is also known in the literature that catalytic hydrogenation of hydrazobenzenes to amines requires vigorous conditions (e.g. high temperature, and/or high pressure, and/or high catalyst intake and/or high acid levels). A study at room temperature and atmospheric pressure with Pd/C, reported in *Catalytic Hydrogenation over Platinum Metals*, P. N. Rylander, Academic Press, New York, 1967, p. 493, shows that a large quantity of acetic acid (30 ml per 2 g azobenzene) will promote the hydrogenation of hydrazobenzene to aniline. Hydrogenation to aniline by Sn/HCl and Zn/HCl is also known in the literature. However, the use of catalytic amounts of acid for hydrogenation has not been reported. So an initial study was done with mixtures of reagent grade aniline and azobenzene to compare an acidic carbon with low levels of acetic acid (1 ml per 150 g azobenzene) and the acidic carbon saturated with phosphoric acid (1 ml per 40 g azobenzene). Hydrogenation times were >60% longer with acetic acid at 125° C. and 24.5 bara vs acidic carbon at 125° C. and 17.6 bara and 280% longer with phosphoric acid at 125° C. and 17.6 bara vs acidic carbon at 125° C. and 17.6 bara. However, all three acids were able to catalyze the reduction of hydrazobenzene to aniline. The superior performance of acidic carbon is surprising, since it was used at the lowest level of the three acids tested. Acidic carbon was then further evaluated for the process.

Azobenzene by-product from pilot plant step (i) coupling reaction was separated from the step (ii) reaction mixture by distillation, then hydrogenated to aniline for recycle to the step (i) reaction. Azobenzene hydrogenation reaction was carried out in a 1 L Parr autoclave with an internal sintered metal filter to allow removal of the finished batch, while retaining the catalyst in the autoclave for the next batch. To start, 200.6 g of the azobenzene containing stream, which was 51–58% azobenzene, was charged to the autoclave with 199.8 g of aniline solvent. Then 1.0 g of 3% Pd/C catalyst (0.315 wt. % bound acidity; 0.006 wt. % free acidity) and 3.0 g of acidic carbon co-catalyst (0.55 wt. % bound acidity; 0.02 wt. % free acidity) were charged to the autoclave. The sealed and stirred autoclave was heated to 175° C., then hydrogen was fed until hydrogen flow rate at 17.6 bara indicated that the reaction was complete. Analysis showed that no azobenzene or hydrazobenzene remained after 43 minutes. The reaction was repeated 23 times by using the catalyst and co-catalyst remaining in the autoclave after purging the batch out through the internal sintered metal filter. There was an addition of 0.1 g of catalyst and 0.3 g of co-catalyst on cycle 14. Analyses showed that azobenzene conversion to aniline for all batches was >98.5% with essentially no hydrazobenzene remaining. Reaction times exceeded 60 minutes on only 4 batches, with the longest time being 67 minutes.

Combined, filtered reaction masses were distilled to recover greater than 90% of the azobenzene as aniline. Residue from the distillation was analyzed by GC/MS and no benzidine was found. Aniline recovered from these lab distillations was used for two lab coupling reactions, without any fresh aniline or other source of recycle aniline. Selectivity from nitrobenzene (94.4% and 95.3%) was comparable to lab reactions with all fresh aniline.

EXAMPLE 16

This example illustrates that the amount of aniline used as solvent for the hydrogenation of azobenzene is not critical, as good results are obtained even with no solvent. Hydrogenations were carried out as described in Example 11, using the same catalyst and acidic carbon co-catalyst. The wt./wt. charge ratio of aniline to distillate containing azobenzene was varied from 0.0 to 1.0. The results in Table 9 indicate no significant effect on reaction time due to the amount of aniline charged.

TABLE 9

| Charge Ratio Aniline/Distillate | Reaction Time minutes |
|---|---|
| 0.0 | 33 |
| 0.25 | 36 |
| 0.5 | 46 |
| 0.75 | 44 |
| 1.0 | 45 |
| 1.0 | 30 |

EXAMPLE 17

This example illustrates that the acidic carbon support of a hydrogenation catalyst can be an effective co-catalyst for hydrogenation of azobenzene, which is contained in the process distillate, to aniline. Therefore, with the right catalyst support it is not necessary to add a separate acidic carbon co-catalyst.

Hydrogenations were carried out by a procedure similar to that described in Example 15, at 180° C. with hydrogen pressure of 7.9 bara. The charges were 400 g of total organics and 1.0 g of a 3% Pd/C catalyst (0.373 wt. % bound acidity; 0.005 wt. % free acidity). There was no separate addition of an acidic carbon co-catalyst. The charge consisted of 270 g of a pilot plant distillate containing azobenzene, 50 g of additional azobenzene and 80 g of aniline. The extra azobenzene was added so that the total azobenzene in the starting reaction mixture would reflect expected level for a commercial plant. A series of eleven batches were made, with ten catalyst recycles. Reaction time for the first two cycles was 25 minutes with 98.3% conversion of azobenzene. For the remaining nine cycles, reaction time varied from 34 to 49 minutes and azobenzene conversion varied from 97.3 to 98.9%. These results are comparable to those reported in Example 11, indicating that the carbon support of the catalyst was by itself sufficient as an acidic carbon co-catalyst.

EXAMPLE 18

This example shows that other catalysts are effective for hydrogenation of azobenzene to aniline. A short catalyst recycle study was carried out with 1 g of a 5% Rh/C catalyst and 3 g of an acidic carbon (0.283 wt. % bound acidity and 0.003 wt. % free acidity). This was carried out without additions of fresh catalyst or co-catalyst. The reaction mixture consisted of 200 g of pilot plant distillate containing azobenzene, 140 g of aniline and 60 g of either azobenzene or hydrazobenzene. The hydrogenation times for Cycles 4 and 5 at 175° C. and 7.9 bara were 40 minutes each, which is comparable to the hydrogenation times of 35 and 44 minutes for Cycles 4 and 5 with 3% Pd/C catalyst at 175° C. and 18.6 bara for the study reported in Example 15. This indicates that Rh/C would be an acceptable catalyst for the azobenzene hydrogenation of this invention process. Other catalysts (such as Pt/C) have not specifically been tested, but it can be expected that they would also be acceptable. In the literature, Pt/C is reported to be similar to Pd/C for azobenzene hydrogenation, although reaction conditions are not reported.

We claim:

1. A process for preparing an optionally substituted 4-aminodiphenylamine comprising:
    (i) reacting an optionally substituted aniline and an optionally substituted nitrobenzene in the presence of water and a base while controlling the amount of water in relation to the base so as to ensure a molar ratio of water to the base charged in the range of not less than about 4:1 at the start of the coupling reaction and not less than about 0.6:1 at the end of the coupling reaction to produce optionally substituted 4-nitrodiphenylamine and/or 4-nitrosodiphenylamine salt;
    (ii) hydrogenating the reaction product of step (i) in the presence of a hydrogenation catalyst and added water so as to ensure a molar ratio of total water to base of at least about 4:1 at the end of hydrogenation;
    (iii) separating the hydrogenation catalyst from the reaction mixture; and
    (iv) obtaining an aqueous phase and organic phase from the reaction mixture, separating the organic phase from the aqueous phase and isolating the optionally substituted 4-aminodiphenylamine from the organic phase.

2. The process of claim 1 wherein in step (i) the molar ratio of water to base is not less than about 4.5:1 at the start and not less than about 1.0:1 at the end of the coupling reaction.

3. The process of claim 1 wherein in step (ii) the molar ratio of total water to base at the reaction end is at least about 6:1.

4. The process of claim 1 wherein in step (i) aniline and nitrobenzene are used and the molar ratio of aniline to nitrobenzene is from about 1:1 to about 10:1.

5. The process of claim 1 wherein in step (i) aniline and nitrobenzene are used and the molar ratio of base to nitrobenzene is from about 0.7:1 to about 4:1.

6. The process of claim 1 wherein optionally substituted nitrobenzene is added to a mixture of optionally substituted aniline, water and base in step (i) and the elapsed time from the start of nitrobenzene addition to the completion of the reaction in step (i) does not exceed about 3.5 hours.

7. The process of claim 1 wherein after the hydrogenation reaction and before separation of the aqueous phase and the organic phase, water is added in an amount sufficient to allow layer separation to take place.

8. The process of claim 1 wherein the aqueous phase from step (iv) containing recycle base is reused to form a subsequent step (i) reaction mixture.

9. The process of claim 1 wherein optionally substituted 4-aminodiphenylamine introduced as an impurity into the step (I) reaction with base and/or aniline recycled to form a step (I) reaction mixture is maintained at a level less than a molar ratio of optionally substituted 4-aminodiphenylamine to optionally substituted nitrobenzene of about 0.05.

10. The process of claim 9 wherein the molar ratio of optionally substituted 4-aminodiphenylamine to optionally substituted nitrobenzene is maintained below about 0.03.

11. The process of claim 1 wherein the hydrogenation catalyst is a supported noble metal catalyst and the amount of new noble metal charged without catalyst recycle is in the range of about 0.01 to about 0.75 milligram atoms per mole of optionally substituted 4-nitrodiphenylamine and/or 4-nitrosodiphenylamine salts.

12. The process of claim 11 wherein the hydrogenation catalyst comprises rhodium on carbon or alumina, ruthenium on carbon or alumina, platinum on carbon or alumina, palladium on carbon or alumina, Raney nickel, Raney copper or mixtures thereof.

13. The process of claim 11 wherein the hydrogenation catalyst comprises platinum on carbon, palladium on carbon or rhodium on carbon.

14. The process of claim 1 wherein the hydrogenation catalyst is recycled and reused in a subsequent step (ii) hydrogentation with fresh catalyst added as needed.

15. The process of claim 14 wherein the weight ratio of recycle catalyst to fresh catalyst introduced into the step (ii) reaction is 1 or higher.

16. The process of claim 14 wherein the hydrogenation catalyst is a supported noble metal catalyst and the amount of fresh catalyst added to the recycled catalyst mass is such that per mole of optionally substituted 4-nitrodiphenylamine and/or 4-nitrosodiphenylamine salts about 0.0 to about 0.4 milligram atoms of new metal are present.

17. The process of claim 1 wherein the hydrogenation time is less than about 4 hours.

18. The process of claim 14 wherein the catalyst, after its separation from the hydrogenation reaction mixture, is washed with water and the washed catalyst is reused in a subsequent step (ii) hydrogenation.

19. The process of claim 18 wherein the catalyst is washed with about 50 to about 500 liters of water per 1.0 kg of catalyst.

20. The process of claim 14 wherein the catalyst, after its separation from the hydrogenation reaction mixture, is kept as a slurry in water before being reused in a subsequent step (ii) hydrogenation.

21. The process of claim 20 wherein the catalyst to water ratio in said slurry is about 0.01 to about 0.25.

22. The process of claim 21 wherein the catalyst to water ratio is about 0.02 to about 0.15.

23. The process of claim 1 wherein a molar excess of optionally substituted aniline is used and the excess optionally substituted aniline is recovered from the organic phase and reused to form a subsequent step (i) reaction mixture.

24. The process of claim 1 wherein aniline and nitrobenzene are used in step (i) and by-product comprising azobenzene and/or azoxybenzene is separated-off from the organic phase from step (iv), said by-product is catalytically hydrogenated to form aniline, and said aniline is reused to form a subsequent step (i) reaction mixture.

25. The process of claim 24 wherein the catalyst used is selected from the same group of catalysts that may be used in step (ii) hydrogenation.

26. The process of claim 24 wherein azobenzene and/or azoxybenzene are distilled from the organic phase from step (iv) and passed to a separate reactor in which they are hydrogenated in the presence of a catalyst and a neutral, weak acid or weak base co-catalyst to form aniline.

27. The process of claim 26 wherein said co-catalyst comprises a weak organic acid from the group comprising acetic acid, stearic acid, octanoic acid or an acidic carbon.

28. The process of claim 27 wherein said acidic carbon has bound acidity.

29. The process of claim 28 wherein said acidic carbon includes the carbon support for a catalyst comprising platinum-on-carbon, palladium-on-carbon or rhodium on carbon.

30. The process of claim 28 wherein said catalyst and co-catalyst are re-used for subsequent batches of azobenzene and/or azoxybenzene containing streams.

31. The process of claim 24 wherein the process conditions for said hydrogenation comprise a temperature from about 70° to 250° C. and a pressure from about 1 to 25 barg.

32. A process for preparing alkylated derivatives of optionally substituted 4-aminodiphenylamines wherein an optionally substituted aniline and an optionally substituted nitrobenzene are reacted and the reaction product is subsequently hydrogenated in accordance with the process of claim 1, after which the optionally substituted 4-aminodiphenylamine so obtained is reductively alkylated to an alkylated derivative of said optionally substituted 4-aminodiphenylamine.

33. The process of claim 1 wherein the temperature at which the step (I) reaction is conducted is about 10° to about 150° C. and the pressure from about 20 to about 200 mbar, the temperature at which the step (ii) reaction is conducted is about 50° to about 150° C. and the pressure from about 1 to about 25 barg.

34. The process of claim 1 wherein said base is a tetraalkylammonium hydroxide.

35. The process of claim 34 wherein said base is selected from the group comprising tetramethylammonium hydroxide, tetrapropylammonium hydroxide, benzyltrimentylammonium hydroxide, tetrabutylammonium hydroxide, phenyltrimethylammonium hydroxide, or carbonate salts of any of the foregoing and mixtures thereof.

36. The process of claim 35 wherein said base is tetramethylammonium hydroxide.

37. The process of claim 1 wherein said substituted aniline is selected from the group comprising 2-methoxyaniline, 4-methoxyaniline, 4-chloroaniline, p-toluidine, 4-nitroaniline, 3-bromoaniline, 3-bromo-4-aminotoluene, p-aminobenzoic acid, 2,4-diaminotoluene, 2,5-dichloroaniline, 1,4-phenylene diamine, 4,4'-methylene dianiline or 1,3,5-triaminobenzene and mixtures thereof.

38. The process of claim 1 wherein said substituted nitrobenzene is selected from the group comprising o- and m-methylnitrobenzene, o- and m-ethylnitrobenzene, or o- and m-methoxynitrobenzene and mixtures thereof.

39. The process of claim 14 wherein the feed to step (ii) is pretreated with used hydrogenation catalyst by contacting said feed with said catalyst under hydrogen at a temperature of from about 50° C. to about 150° C. and a hydrogen pressure of from about 1 to about 25 barg.

40. A process for preparing 4-aminodiphenylamine comprising:

(i) reacting aniline and nitrobenzene in the presence of water and a base while controlling the amount of water in relation to the base so as to ensure a molar ratio of water to the base charged of not less than about 4:1 at the start of the coupling reaction and not less than about 0.6:1 at the end of the coupling reaction to produce 4-nitrodiphenylamine and/or 4-nitrosodiphenylamine salt;

(ii) hydrogenating the reaction product of step (i) in the presence of a hydrogenation catalyst and added water so as to ensure a molar ratio of total water to base of at least about 4:1 at the end of hydrogenation;

(iii) separating the hydrogenation catalyst from the reaction mixture;

(iv) obtaining an aqueous phase and organic phase from the reaction mixture, separating the organic phase from the aqueous phase and isolating 4-aminodiphenylamine from the organic phase;

(v) reusing the aqueous phase to form a subsequent step (i) reaction mixture;

(vi) reusing the hydrogenation catalyst in a subsequent step (ii) hydrogenation; and (vii) hydrogenating azobenzene and/or azoxybenzene which may be produced during step (I) and/or step (ii) to aniline and isolating the aniline for reuse in a subsequent step (i) reaction mixture together with excess aniline that may be recovered from the organic phase in step (iv).

\* \* \* \* \*